US007252976B2

(12) United States Patent  (10) Patent No.: US 7,252,976 B2
Lin et al.  (45) Date of Patent: Aug. 7, 2007

(54) QUANTITATIVE RT-PCR TO AC133 TO DIAGNOSE CANCER AND MONITOR ANGIOGENIC ACTIVITY IN A CELL SAMPLE

(75) Inventors: Edward H. Lin, Houston, TX (US); Xifeng Wu, Pearland, TX (US); Keping Xie, Pearland, TX (US)

(73) Assignee: Board of Regents the University of Texas System, Austin, TX (US)

( * ) Notice: Subject to any disclaimer, the term of this patent is extended or adjusted under 35 U.S.C. 154(b) by 424 days.

(21) Appl. No.: 10/618,102

(22) Filed: Jul. 11, 2003

(65) Prior Publication Data

US 2004/0086915 A1 May 6, 2004

Related U.S. Application Data

(60) Provisional application No. 60/406,535, filed on Aug. 28, 2002.

(51) Int. Cl.
*C12P 19/34* (2006.01)
*C12Q 1/68* (2006.01)
*C07H 21/04* (2006.01)

(52) U.S. Cl. .................. 435/91.2; 435/6; 536/23.1; 536/24.3

(58) Field of Classification Search ..................... None
See application file for complete search history.

(56) References Cited

U.S. PATENT DOCUMENTS

| 5,776,154 | A | 7/1998 | Taylor et al. ............ 606/167 |
| 5,843,633 | A | 12/1998 | Yin et al. ................ 435/2 |
| 6,037,129 | A | 3/2000 | Cole et al. ............... 435/6 |
| 6,329,179 | B1 | 12/2001 | Kopreski ................ 435/91.2 |
| 6,455,678 | B1 | 9/2002 | Yin et al. ............... 530/395 |
| 2002/0076707 | A1 | 6/2002 | Mack et al. ............. 435/6 |

FOREIGN PATENT DOCUMENTS

| WO | WO 97/41224 | 11/1997 |
| WO | WO 00/55633 | 9/2000 |
| WO | WO 02/059271 | 8/2002 |

OTHER PUBLICATIONS

Asahara et al., "VEGF contributes to postnasal neovascularization by mobilizing bone marrow-drived endothelial progenitor cells," *EMBO J.*, 18(14):3964-3972, 1999.
Bhatia, "AC133 expression in human stem cells," *Leukemia*, 15(11):, 1685-1688, 2001.
Boyer et al., "Isolation of endothelial cells and their progenitor cells from human peripheral blood," *J. Vasc. Surg.*, 31(1-1):181-189, 2000.
Buhring et al., "AC133 antigen expression is not restricted to acute myeloid leukemia blasts but is also found on acute lymphoid leukemia blasts and on a subset of CD34+ B-cell precursosrs," *Blood*, 94(2):832-833, 1999.

Byrne and Bundred, "Surrogate markers of tumoral angiogenesis," *Biological Markers*, 15(4):334-339, 2000.
Corbeil et al., "The human AC133 hematopoeitic stem cell antigen is also expressed in epithelial cells and targeted to plasma membrane protrusions," *Journal of Biological Chemistry*, 275(8):5512-5520, 2000.
Dimitriou et al., "In vitro proliferative and differentiating characteristics of CD133(+) and CD34(+) cord blood cells in the presence of thrombopoietin (TPO) or erythropoietin (EPO): potential implications for hematopoeitic cell transplantation," *Leukemia Research*, 27(12):1143-1151, 2003.
Folkman et al., "Angiogenesis research: guidelines for translation to clinical application," *Thrombosis Haemostasis*, 86:23-33, 2001.
Forraz et al., "AC133+ umbilical cord blood progenitor demonstrate rapid self-renewal and low apoptosis," *British Journal of Haematology*, 119(2):516-524, 2002.
Gill et al., "Vascular trama induces rapid but transient mobilization of VEGFR2+AC133+ Endothelial precursor cells," *Circ. Res.*, 88(2):167-174, 2001.
Handgretinger et al., "Biology and plasticity of CD133+ hematopoietic stem cells," *Annals of the New York Academy of Sciences*, 996:141-151, 2003.
Hariharan et al., "Human immunodeficiency virus infection of human placental cord blood CD34+AC133+ stem cells and their progeny," *AIDS Res. Hum. Retroviruses*, 15(17):1545-1552, 1999.
Hurvitz et al., "Bevacizumab (a monoclonal antibody to vascular endothelial growth factor) prolongs survival in first-line colorectal cancer(CRC): results of a phase III trial of bevacizumab in combination with bolus IFL (irinotecan, 5-flurouracil, leucovorin) as a first-line therapy in subjects with metastatic CRC," PRO ASCO Conference, Chicago, Ill., abst #3536, 2003.
Kanayasu-Toyoda et al., "CD31 (PECAM-1)-bright cells derived from AC133-positive cells in human peripheral blood as endothelial-precursor cells," *Journal of Cellular Physiology*, 195(1):119-129, 2003.
Lee et al., AC133 antigen as a prognostic factor in acute leukemia, *Leukemia Research*, 25(9):757-767, 2001.
Marchetti et al., "Prediction of survival in stage I lung carcinoma patients by telomerase function evaluation," *Lab. Invest.*, 82(6), 2002.
Miraglia et al., "A response to AC133 hematopoietic stem cell antigen: human homologue of mouse kidney prominin or distinct member of a novel protein family?" *Blood*, 91(11):4390-4391, 1998.
Mundhenke et al., "Tissue examination to monitor antiangiogenic therapy: a phase I clinical trial with endostatin," *Clinical Cancer Res.*, 7:3366-3374, 2001.
Nakatani et al., "Circulating endothelial cells in Kawasaki disease," *Clinical & Experimental Immunology*, 131(3):536-540, 2003.
Reyes et al., "Origin of endothelial progenitors in human postnatal bone marrow," *J. Clin. Invest.*, 109(3):337-346, 2002.
Reyes et al., "Purification and ex vivo expansion of postnasal human marrow mesodermal progenitor cells," *Blood*, 98(9):2615-2625, 2001.

(Continued)

*Primary Examiner*—Teresa E. Strzelecka
(74) *Attorney, Agent, or Firm*—Fulbright & Jaworski L.L.P.

(57) ABSTRACT

The present invention involves the use of quantitative RT-PCR to identify AC133 as a marker. AC133 is prevalent on endothelial progenitor cells (EPCs), which are important cells in angiogenesis. Therefore, the invention is applied to ascertain the quantity of EPCs in a subject, and to diagnose and monitor angiogenesis, for example, in injured tissues and in cancer development and progression.

9 Claims, 5 Drawing Sheets

OTHER PUBLICATIONS

Salven et al., "VEGFR-3 and CD 133 identify a population of CD34+ lymphatic/vascular endothelial precursor cells," *Blood*, 101(1):168-172, 2003.

Schmeisser et al., "Monocytes coexpress endothelial and macrophagocytic linkage markers and form cord-like structures in Matrigel under angiogenic conditions," *Cardiovascular Res.*, 49:671-680, 2001.

Shi et al., "Influence of nitric oxide synthase II gene disruption on tumor growth and metastasis," *Cancer Res.*, 60:2579-2583, 2000.

Shi et al., "Regulation of vascular endothelial growth factor expression by acidosis in human cancer cells," *Oncogene*, 20:3751-3761, 2001.

Singh et al., "Identification of a cancer stem cell in human brain tumors," *Cancer Res.*, 63:5821-5828, 2003.

Ueda et al., "DNA microarray analysis of stage progression mechanism in myelodysplastic syndrome," *British Journal of Haematology*, 123(2):288-296, 2003.

Vercauteren et al., "CD133 (AC133) expression on AML cells and progenitors," *Cytotherapy*, 3(6):449-459, 2001.

Xu et al., "One-step analysis and quantification of RNA by RT-PCR: using high-temperature reverse transcription," *Focus*, 22(1):3-5, 2000.

Yin et al., "AC133, a novel marker for human hematopoietic stem and progenitor cells," *Blood*, 90(12):5002-5012, 1997.

Yu et al., "AC133-2, a novel isoform of human AC133 stem cell antigen," *Journal of Biological Chemistry*, 277(23):20711-20716, 2002.

Mehra et al., "Progenitor marker CD133 mRNA is elevated in peripheral blood of cancer patients with bone metastases," *Clin. Cancer Res.*, 12:4859-4866, 2006.

Gallacher et al., "Isolation and characterization of human CD34-Lin- and CD34+ Lin-hematopoietic stem cells using cell surface markers AC133 and CD7," *Blood*, 95:2813-2820, 2000.

SEQUENCE LISTING

```
<160> NUMBER OF SEQ ID NOS: 14

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
tgtacgaatt cgacagctac ttggctcaga c                              31

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
tctagctcga gcatgatctt tatgataacc                                30

<210> SEQ ID NO 3
<211> LENGTH: 3794
<212> TYPE: DNA
<213> ORGANISM: Homo sapiens
<220> FEATURE:
<221> NAME/KEY: CDS
<222> LOCATION: (38)..(2635)

<400> SEQUENCE: 3
ccaagttcta cctcatgttt ggaggatctt gctagct atg gcc ctc gta ctc ggc      55
                                        Met Ala Leu Val Leu Gly
                                        1               5 tcc ctg ttg ctg ctg ggg ctg tgc ggg aac tcc ttt tca gga ggg cag     103
Ser Leu Leu Leu Leu Gly Leu Cys Gly Asn Ser Phe Ser Gly Gly Gln
             10                  15                  20 cct tca tcc aca gat gct cct aag gct tgg aat tat gaa ttg cct gca     151
Pro Ser Ser Thr Asp Ala Pro Lys Ala Trp Asn Tyr Glu Leu Pro Ala
         25                  30                  35 aca aat tat gag acc caa gac tcc cat aaa gct gga ccc att ggc att     199
Thr Asn Tyr Glu Thr Gln Asp Ser His Lys Ala Gly Pro Ile Gly Ile
     40                  45                  50 ctc ttt gaa cta gtg cat atc ttt ctc tat gtg gta cag ccg cgt gat     247
Leu Phe Glu Leu Val His Ile Phe Leu Tyr Val Val Gln Pro Arg Asp
55                  60                  65                  70 ttc cca gaa gat act ttg aga aaa ttc tta cag aag gca tat gaa tcc     295
Phe Pro Glu Asp Thr Leu Arg Lys Phe Leu Gln Lys Ala Tyr Glu Ser
```

|  |  |
|---|---|
| aaa att gat tat gac aag cca gaa act gta atc tta ggt cta aag att<br>Lys Ile Asp Tyr Asp Lys Pro Glu Thr Val Ile Leu Gly Leu Lys Ile<br>          90                      95                    100 | 343 |
| gtc tac tat gaa gca ggg att att cta tgc tgt gtc ctg ggg ctg ctg<br>Val Tyr Tyr Glu Ala Gly Ile Ile Leu Cys Cys Val Leu Gly Leu Leu<br>         105                     110                    115 | 391 |
| ttt att att ctg atg cct ctg gtg ggg tat ttc ttt tgt atg tgt cgt<br>Phe Ile Ile Leu Met Pro Leu Val Gly Tyr Phe Phe Cys Met Cys Arg<br>120                     125                     130 | 439 |
| tgc tgt aac aaa tgt ggt gga gaa atg cac cag cga cag aag gaa aat<br>Cys Cys Asn Lys Cys Gly Gly Glu Met His Gln Arg Gln Lys Glu Asn<br>135                140                    145                  150 | 487 |
| ggg ccc ttc ctg agg aaa tgc ttt gca atc tcc ctg ttg gtg att tgt<br>Gly Pro Phe Leu Arg Lys Cys Phe Ala Ile Ser Leu Leu Val Ile Cys<br>               155                     160                    165 | 535 |
| ata ata ata agc att ggc atc ttc tat ggt ttt gtg gca aat cac cag<br>Ile Ile Ile Ser Ile Gly Ile Phe Tyr Gly Phe Val Ala Asn His Gln<br>         170                     175                    180 | 583 |
| gta aga acc cgg atc aaa agg agt cgg aaa ctg gca gat agc aat ttc<br>Val Arg Thr Arg Ile Lys Arg Ser Arg Lys Leu Ala Asp Ser Asn Phe<br>               185                     190                    195 | 631 |
| aag gac ttg cga act ctc ttg aat gaa act cca gag caa atc aaa tat<br>Lys Asp Leu Arg Thr Leu Leu Asn Glu Thr Pro Glu Gln Ile Lys Tyr<br>200                   205                    210 | 679 |
| ata ttg gcc cag tac aac act acc aag gac aag gcg ttc aca gat ctg<br>Ile Leu Ala Gln Tyr Asn Thr Thr Lys Asp Lys Ala Phe Thr Asp Leu<br>215                     220                    225                  230 | 727 |
| aac agt atc aat tca gtg cta gga ggc gga att ctt gac cga ctg aga<br>Asn Ser Ile Asn Ser Val Leu Gly Gly Gly Ile Leu Asp Arg Leu Arg<br>               235                     240                    245 | 775 |
| ccc aac atc atc cct gtt ctt gat gag att aag tcc atg gca aca gcg<br>Pro Asn Ile Ile Pro Val Leu Asp Glu Ile Lys Ser Met Ala Thr Ala<br>         250                     255                    260 | 823 |
| atc aag gag acc aaa gag gcg ttg gag aac atg aac agc acc ttg aag<br>Ile Lys Glu Thr Lys Glu Ala Leu Glu Asn Met Asn Ser Thr Leu Lys<br>               265                     270                    275 | 871 |
| agc ttg cac caa caa agt aca cag ctt agc agc agt ctg acc agc gtg<br>Ser Leu His Gln Gln Ser Thr Gln Leu Ser Ser Ser Leu Thr Ser Val<br>280                     285                    290 | 919 |
| aaa act agc ctg cgg tca tct ctc aat gac cct ctg tgc ttg gtg cat<br>Lys Thr Ser Leu Arg Ser Ser Leu Asn Asp Pro Leu Cys Leu Val His<br>295                     300                    305                  310 | 967 |
| cca tca agt gaa acc tgc aac agc atc aga ttg tct cta agc cag ctg<br>Pro Ser Ser Glu Thr Cys Asn Ser Ile Arg Leu Ser Leu Ser Gln Leu<br>               315                     320                    325 | 1015 |
| aat agc aac cct gaa ctg agg cag ctt cca ccc gtg gat gca gaa ctt<br>Asn Ser Asn Pro Glu Leu Arg Gln Leu Pro Pro Val Asp Ala Glu Leu<br>         330                     335                    340 | 1063 |
| gac aac gtt aat aac gtt ctt agg aca gat ttg gat ggc ctg gtc caa<br>Asp Asn Val Asn Asn Val Leu Arg Thr Asp Leu Asp Gly Leu Val Gln<br>               345                     350                    355 | 1111 |
| cag ggc tat caa tcc ctt aat gat ata cct gac aga gta caa cgc caa<br>Gln Gly Tyr Gln Ser Leu Asn Asp Ile Pro Asp Arg Val Gln Arg Gln<br>360                     365                    370 | 1159 |
| acc acg act gtc gta gca ggt atc aaa agg gtc ttg aat tcc att ggt<br>Thr Thr Thr Val Val Ala Gly Ile Lys Arg Val Leu Asn Ser Ile Gly<br>375                     380                    385                  390 | 1207 |
| tca gat atc gac aat gta act cag cgt ctt cct att cag gat ata ctc | 1255 |

| | | | | | | | | | | | | | | |
|---|---|---|---|---|---|---|---|---|---|---|---|---|---|---|
| Ser | Asp | Ile | Asp | Asn | Val | Thr | Gln | Arg | Leu | Pro | Ile | Gln | Asp | Ile | Leu |
| | | | 395 | | | | 400 | | | | | 405 | | | |

```
tca gca ttc tct gtt tat gtt aat aac act gaa agt tac atc cac aga     1303
Ser Ala Phe Ser Val Tyr Val Asn Asn Thr Glu Ser Tyr Ile His Arg
            410                 415                 420 aat tta cct aca ttg gaa gag tat gat tca tac tgg tgg ctg ggt ggc     1351
Asn Leu Pro Thr Leu Glu Glu Tyr Asp Ser Tyr Trp Trp Leu Gly Gly
        425                 430                 435 ctg gtc atc tgc tct ctg ctg acc ctc atc gtg att ttt tac tac ctg     1399
Leu Val Ile Cys Ser Leu Leu Thr Leu Ile Val Ile Phe Tyr Tyr Leu
    440                 445                 450 ggc tta ctg tgt ggc gtg tgc ggc tat gac agg cat gcc acc ccg acc     1447
Gly Leu Leu Cys Gly Val Cys Gly Tyr Asp Arg His Ala Thr Pro Thr
455                 460                 465                 470 acc cga ggc tgt gtc tcc aac acc gga ggc gtc ttc ctc atg gtt gga     1495
Thr Arg Gly Cys Val Ser Asn Thr Gly Gly Val Phe Leu Met Val Gly
                475                 480                 485 gtt gga tta agt ttc ctc ttt tgc tgg ata ttg atg att gtg gtt         1543
Val Gly Leu Ser Phe Leu Phe Cys Trp Ile Leu Met Ile Ile Val Val
            490                 495                 500 ctt acc ttt gtc ttt ggt gca aat gtg gaa aaa ctg atc tgt gaa cct     1591
Leu Thr Phe Val Phe Gly Ala Asn Val Glu Lys Leu Ile Cys Glu Pro
        505                 510                 515 tac acg agc aag gaa tta ttc cgg gtt ttg gat aca ccc tac tta cta     1639
Tyr Thr Ser Lys Glu Leu Phe Arg Val Leu Asp Thr Pro Tyr Leu Leu
    520                 525                 530 aat gaa gac tgg gaa tac tat ctc tct ggg aag cta ttt aat aaa tca     1687
Asn Glu Asp Trp Glu Tyr Tyr Leu Ser Gly Lys Leu Phe Asn Lys Ser
535                 540                 545                 550 aaa atg aag ctc act ttt gaa caa gtt tac agt gac tgc aaa aaa aat     1735
Lys Met Lys Leu Thr Phe Glu Gln Val Tyr Ser Asp Cys Lys Lys Asn
                555                 560                 565 aga ggc act tac ggc act ctt cac ctg cag aac agc ttc aat atc agt     1783
Arg Gly Thr Tyr Gly Thr Leu His Leu Gln Asn Ser Phe Asn Ile Ser
            570                 575                 580 gaa cat ctc aac att aat gag cat act gga agc ata agc agt gaa ttg     1831
Glu His Leu Asn Ile Asn Glu His Thr Gly Ser Ile Ser Ser Glu Leu
        585                 590                 595 gaa agt ctg aag gta aat ctt aat atc ttt ctg ttg ggt gca gca gga     1879
Glu Ser Leu Lys Val Asn Leu Asn Ile Phe Leu Leu Gly Ala Ala Gly
    600                 605                 610 aga aaa aac ctt cag gat ttt gct gct tgt gga ata gac aga atg aat     1927
Arg Lys Asn Leu Gln Asp Phe Ala Ala Cys Gly Ile Asp Arg Met Asn
615                 620                 625                 630 tat gac agc tac ttg gct cag act ggt aaa tcc ccc gca gga gtg aat     1975
Tyr Asp Ser Tyr Leu Ala Gln Thr Gly Lys Ser Pro Ala Gly Val Asn
                635                 640                 645 ctt tta tca ttt gca tat gat cta gaa gca aaa gca aac agt ttg ccc     2023
Leu Leu Ser Phe Ala Tyr Asp Leu Glu Ala Lys Ala Asn Ser Leu Pro
            650                 655                 660 cca gga aat ttg agg aac tcc ctg aaa aga gat gca caa act att aaa     2071
Pro Gly Asn Leu Arg Asn Ser Leu Lys Arg Asp Ala Gln Thr Ile Lys
        665                 670                 675 aca att cac cag caa cga gtc ctt cct ata gaa caa tca ctg agc act     2119
Thr Ile His Gln Gln Arg Val Leu Pro Ile Glu Gln Ser Leu Ser Thr
    680                 685                 690 cta tac caa agc gtc aag ata ctt caa cgc aca ggg aat gga ttg ttg     2167
Leu Tyr Gln Ser Val Lys Ile Leu Gln Arg Thr Gly Asn Gly Leu Leu
695                 700                 705                 710
```

```
                                          -continued
gag aga gta act agg att cta gct tct ctg gat ttt gct cag aac ttc    2215
Glu Arg Val Thr Arg Ile Leu Ala Ser Leu Asp Phe Ala Gln Asn Phe
            715                 720                 725 atc aca aac aat act tcc tct gtt att att gag gaa act aag aag tat    2263
Ile Thr Asn Asn Thr Ser Ser Val Ile Ile Glu Glu Thr Lys Lys Tyr
        730                 735                 740 ggg aga aca ata ata gga tat ttt gaa cat tat ctg cag tgg atc gag    2311
Gly Arg Thr Ile Ile Gly Tyr Phe Glu His Tyr Leu Gln Trp Ile Glu
    745                 750                 755 ttc tct atc agt gag aaa gtg gca tcg tgc aaa cct gtg gcc acc gct    2359
Phe Ser Ile Ser Glu Lys Val Ala Ser Cys Lys Pro Val Ala Thr Ala
760                 765                 770 cta gat act gct gtt gat gtc ttt ctg tgt agc tac att atc gac ccc    2407
Leu Asp Thr Ala Val Asp Val Phe Leu Cys Ser Tyr Ile Ile Asp Pro
775                 780                 785                 790 ttg aat ttg ttt tgg ttt ggc ata gga aaa gct act gta ttt tta ctt    2455
Leu Asn Leu Phe Trp Phe Gly Ile Gly Lys Ala Thr Val Phe Leu Leu
                795                 800                 805 ccg gct cta att ttt gcg gta aaa ctg gct aag tac tat cgt cga atg    2503
Pro Ala Leu Ile Phe Ala Val Lys Leu Ala Lys Tyr Tyr Arg Arg Met
            810                 815                 820 gat tcg gag gac gtg tac gat gat gtt gaa act ata ccc atg aaa aat    2551
Asp Ser Glu Asp Val Tyr Asp Asp Val Glu Thr Ile Pro Met Lys Asn
        825                 830                 835 atg gaa aat ggt aat aat ggt tat cat aaa gat cat gta tat ggt att    2599
Met Glu Asn Gly Asn Asn Gly Tyr His Lys Asp His Val Tyr Gly Ile
    840                 845                 850 cac aat cct gtt atg aca agc cca tca caa cat tga tagctgatgt         2645
His Asn Pro Val Met Thr Ser Pro Ser Gln His
855                 860                 865 tgaaactgct tgagcatcag gatactcaaa gtggaaagga tcacagattt ttggtagttt   2705
ctgggtctac aaggactttc caaatccagg agcaacgcca gtggcaacgt agtgactcag   2765
gcgggcacca aggcaacggc accattggtc tctgggtagt gctttaagaa tgaacacaat   2825
cacgttatag tccatggtcc atcactattc aaggatgact ccctcccttc ctgtctattt   2885
ttgtttttta cttttttaca ctgagtttct atttagacac tacaacatat ggggtgtttg   2945
ttcccattgg atgcatttct atcaaaactc tatcaaatgt gatggctaga ttctaacata   3005
ttgccatgtg tggagtgtgc tgaacacaca ccagtttaca ggaaagatgc attttgtgta   3065
cagtaaacgg tgtatatacc ttttgttacc acagagtttt ttaaacaaat gagtattata   3125
ggactttctt ctaaatgagc taaataagtc accattgact tcttggtgct gttgaaaata   3185
atccattttc actaaaagtg tgtgaaacct acagcatatt cttcacgcag agattttcat   3245
ctattatact ttatcaaaga ttggccatgt tccacttgga aatggcatgc aaaagccatc   3305
atagagaaac ctgcgtaact ccatctgaca aattcaaaag agagagagag atcttgagag   3365
agaaatgctg ttcgttcaaa agtggagttg ttttaacaga tgccaattac ggtgtacagt   3425
ttaacagagt tttctgttgc attaggataa acattaattg gagtgcagct aacatgagta   3485
tcatcagact agtatcaagt gttctaaaat gaaatatgag aagatcctgt cacaattctt   3545
agatctggtg tccagcatgg atgaaacctt tgagtttggt ccctaaattt gcatgaaagc   3605
acaaggtaaa tattcatttg cttcaggagt ttcatgttgg atctgtcatt atcaaaagtg   3665
atcagcaatg aagaactggt cggacaaaat ttaacgttga tgtaatggaa ttccagatgt   3725
aggcattccc cccaggtctt ttcatgtgca gattgcagtt ctgattcatt tgaataaaaa   3785
ggaacttgg                                                          3794
```

<210> SEQ ID NO 4
<211> LENGTH: 865
<212> TYPE: PRT
<213> ORGANISM: Homo sapiens

<400> SEQUENCE: 4

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
        355                 360                 365

Asp Arg Val Gln Arg Gln Thr Thr Thr Val Val Ala Gly Ile Lys Arg
```

-continued

```
                370                 375                 380
Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
                420                 425                 430

Tyr Trp Trp Leu Gly Gly Leu Val Ile Cys Ser Leu Leu Thr Leu Ile
                435                 440                 445

Val Ile Phe Tyr Tyr Leu Gly Leu Leu Cys Gly Val Cys Gly Tyr Asp
450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
                500                 505                 510

Lys Leu Ile Cys Glu Pro Tyr Thr Ser Lys Glu Leu Phe Arg Val Leu
                515                 520                 525

Asp Thr Pro Tyr Leu Leu Asn Glu Asp Trp Glu Tyr Tyr Leu Ser Gly
530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
                580                 585                 590

Ser Ile Ser Ser Glu Leu Glu Ser Leu Lys Val Asn Leu Asn Ile Phe
                595                 600                 605

Leu Leu Gly Ala Ala Gly Arg Lys Asn Leu Gln Asp Phe Ala Ala Cys
                610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
                660                 665                 670

Asp Ala Gln Thr Ile Lys Thr Ile His Gln Gln Arg Val Leu Pro Ile
                675                 680                 685

Glu Gln Ser Leu Ser Thr Leu Tyr Gln Ser Val Lys Ile Leu Gln Arg
                690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Thr Ser Ser Val Ile Ile
                725                 730                 735

Glu Glu Thr Lys Lys Tyr Gly Arg Thr Ile Ile Gly Tyr Phe Glu His
                740                 745                 750

Tyr Leu Gln Trp Ile Glu Phe Ser Ile Ser Glu Lys Val Ala Ser Cys
                755                 760                 765

Lys Pro Val Ala Thr Ala Leu Asp Thr Ala Val Asp Val Phe Leu Cys
                770                 775                 780

Ser Tyr Ile Ile Asp Pro Leu Asn Leu Phe Trp Phe Gly Ile Gly Lys
785                 790                 795                 800
```

-continued

```
Ala Thr Val Phe Leu Leu Pro Ala Leu Ile Phe Ala Val Lys Leu Ala
            805                 810                 815
Lys Tyr Tyr Arg Arg Met Asp Ser Glu Asp Val Tyr Asp Asp Val Glu
        820                 825                 830
Thr Ile Pro Met Lys Asn Met Glu Asn Gly Asn Asn Gly Tyr His Lys
    835                 840                 845
Asp His Val Tyr Gly Ile His Asn Pro Val Met Thr Ser Pro Ser Gln
850                 855                 860
His
865

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
agccttcatc cacagatgct                                                   20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ttttggattc atatgccttc tg                                                22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
cttcaccacc atggagaagg c                                                 21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ggcatggact gtggtcatga g                                                 21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
```

```
catgtttgga ggatcttgct agc                                              23

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
ttcccgcaca gcccc                                                       15

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
atggccctcg tactcggctc cc                                               22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
cttcaccacc atggagaagg c                                                21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
ggcatggact gtggtcatga g                                                21

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
cctggccaag gtcatccatg acaactttt                                        28
```

QUANTITATIVE RT-PCR TO AC133 TO DIAGNOSE CANCER AND MONITOR ANGIOGENIC ACTIVITY IN A CELL SAMPLE

The present invention claims priority to co-pending application U.S. Provisional Patent Application Ser. No. 60/406,535 filed on Aug. 28, 2002. The entire text of the above-referenced disclosure is specifically incorporated herein by reference without disclaimer.

BACKGROUND OF THE INVENTION

1. Field of the Invention

The invention relates to the fields of cancer biology and nucleic acid biochemistry. Specifically, this invention provides a new method for diagnosing cancer and monitoring angiogenic activity through the amplification and quantitation of a particular gene product indicative of angiogenic activity.

2. Description of Related Art

Over forty target anti-angiogenic agents have been introduced into Phase I, II and III clinical trials in cancer and other non-cancer disease. Cytotoxic agents also possess anti-angiogenic activities. The clinical results from a number of lead anti-angiogenic agents have been disappointing despite their remarkable successes in animal models (Mundhenke et al., 2001). Only until recently, a randomized phase III study showed for the first time that adding bevacezumab, an antiVEGF antibody, to 5-FU, leucovorin, irinotecan (IFL) in metastatic colorectal cancer patients improved tumor response rate, time to tumor progression and overall survival as compared with IFL alone (Hurvitz et al., 2003). Therefore, monitoring and validating anti-angiogenic target response with a defined surrogate(s) would be of paramount clinical importance (Mundhenke et al., 2001; Folkman et al. 2001). Many techniques presently in use are impractical, invasive, and uneconomical.

Microvessel density assay (MVD), the most widely used angiogenesis surrogate, is quantified by counting the density of CD34+ endothelial cells distributed within the tumor (Byrne and Bundred, 2000). MVD has many practical and theoretical limitations for clinical use, however, as it requires direct assessment of microvessels within the tumor tissue. Thus, MVD is invasive and would not be suitable for serial measurements. Furthermore, tumor angiogenesis is enormously heterogeneous, as microvessel density is much higher in the periphery than in the center of an established tumor mass. In addition, MVD overlooks the systemic effects of angiogenic cytokines and, more importantly, endothelial progenitors.

Angiogenesis occurs not only through tumor vessel cooption, but also through mobilization and activation of bone marrow derived endothelial progenitor cells (EPCs) to the sites of active angiogenesis, an increasingly recognized key feature of postnatal angiogenesis, and a feature which MVD assays fail to assess (Asahara et al., 1999). Therefore, EPCs are viable angiogenic surrogates and could be quantified with fluorescence-activated cell sorting techniques (FACS) a using monoclonal antibodies.

However, the FACS procedure has many limitations. For instance, because EPCs are found in low concentrations and also give a poor yield during isolation, FACS assays require up to 50–100 mL of blood per assay. This process can be quite burdensome if serial measurements are required. FACS can be highly variable and subject to poor yield and viability of EPCs, as it is believed that EPCs often undergo apoptosis during isolation procedures, further lowering their recovery. In addition, the FACS procedure is cumbersome, and requires an expensive FACS sorter and an experienced technician to run the machine.

Therefore, there is a need for anti-angiogenic surrogate markers that meet the following specifications for clinical use: (1) they should be non-invasive, accessible and reproducible; (2) they should be feasible for serial measurement and economical; and (3) most importantly, they should mirror the underlying tumor angiogenic activities (Byrne and Bundred, 2000).

SUMMARY OF THE INVENTION

The present invention provides methods for detecting the underlying angiogenic activity due to cancer or inflammatory states that activate angiogenesis. In particular embodiments, the present invention provides methods for the diagnosis of cancer in a subject comprising: (a) obtaining a sample comprising cells of the subject; (b) obtaining RNA transcripts from cells of the sample; (c) performing quantitative PCR on the RNA using primers that amplify an AC133 nucleic acid segment; and (d) comparing the amount of AC133 amplification product in cells from cancer subjects with the amount of amplification product in cells from non-cancer subjects, wherein an increase in the amount of AC133 amplification product in cells of the cancer subject, as compared to the amount of AC133 amplification product from cells in non-cancer subjects, indicates that the subject has cancer. The quantitative PCR may be semi-quantitative or fully quantitative. This method may be used to indicate underlying angiogenic activity from cancer.

In particular embodiments, the method can be used to diagnose cancers including, but not limited to colorectal cancer, bladder cancer, ovarian cancer, testicular cancer, breast cancer, skin cancer, lung cancer, pancreatic cancer, stomach cancer, esophageal cancer, brain cancer, leukemia, liver cancer, endometrial cancer, prostate cancer, and head and neck cancer. In other particular embodiments, the cancer is a non-epithelial cancer. In more particular embodiments, the non-epithelial cancer is a bone sarcoma, a soft tissue sarcoma, or a gastrointestinal stromal tumor.

In one embodiment of the invention, the cells are mononuclear. In other specific embodiments, the cells are isolated from a human subject previously diagnosed with cancer. In other embodiments, the sample is blood taken from the peripheral circulatory system.

In other specific aspects of the invention, the forward primer is composed of the DNA sequence 5'-tgtacgaattcgacagctacttggctcagac-3' (SEQ ID NO:1). In another specific aspect of the invention, the reverse primer is composed of the DNA sequence 5'-tctagctcgagcatgatctttatgataacc-3' (SEQ ID NO:2).

In other embodiments of the invention, the increase of AC133 amplification product further predicts tumor burden. In another embodiment of the invention, the increase of AC133 amplification product further predicts tumor relapse. In another embodiment of the invention, the invention further comprises making a treatment decision based on the increase in the amount of AC133 amplification product in the cells of the subject.

In certain defined embodiments of the present invention, the method further involves treating the subject for cancer. More specifically, another specific embodiment of the invention is to treat the subject with radiotherapy, immunotherapy, chemotherapy, hormonal therapy or gene therapy. The method may also involve monitoring the angiogenic effects of cancer therapy involving radiotherapy, immunotherapy, chemotherapy, hormonal therapy or gene therapy.

In another embodiment, the invention provides methods to quantify endothelial progenitor cells in a sample comprising: (a) obtaining a sample comprising cells of the subject; (b) obtaining RNA transcripts from cells of the sample; and (c) performing quantitative PCR using primers that amplify an AC133 nucleic acid segment, wherein the amount of AC133 amplification product in cells of the sample, as compared to a standardized curve, estimates the total quantity of the endothelial progenitor cells in the sample. In a specific embodiment, the standardized curve is derived from serial dilution of known quantities of said bone marrow-derived endothelial progenitor cells. In a specific aspect of the invention, the accuracy of the determination is 99%. In another aspect of the invention, the detection limit is one endothelial progenitor cell per one million cells.

Also provided herein is a method for monitoring angiogenic activity in cells of a subject comprising: (a) obtaining a sample comprising cells of the subject; (b) obtaining RNA transcripts from cells of the sample; (c) performing quantitative PCR™ using primers that amplify an AC133 nucleic acid segment; and (d) assessing the amount of AC133 amplification product, wherein the amount of AC133 amplification product in cells of the subject is an indicator of the angiogenic activity in cells of the subject. In a specific embodiment of the invention, the sample is blood taken from the peripheral circulatory system. In another embodiment, the invention further comprises assessing the amount of circulating endothelial cells. In a specific embodiment, the invention further comprises assessing VEGF levels in the sample. In another embodiment, the invention comprises developing an angiogenic profile of the subject.

In a specific embodiment of the invention, the invention is used to detect the presence of vascular injury, autoimmune disease, myocardial infarction or sepsis. In another aspect of the invention, the subject has previously been administered an anti-angiogenic therapy, and the assessing comprises assessing the efficacy of the anti-angiogenic therapy.

In the context of the present document, including the claims, the words "a" and "an", when used with the conjunction "comprising" denote "one or more."

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
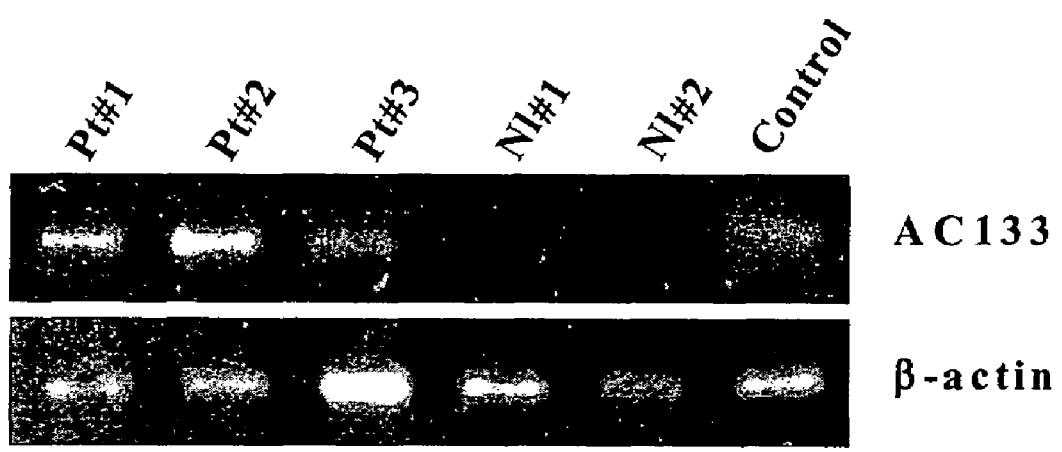
FIG. 1. PCR™ of AC133. Mononuclear cells were isolated from peripheral blood by the Ficoll-Paque (Pharmacia Biotech) procedure. RNA was extracted using Trizol reagent (Gibco Life Technologies) and its concentration was measured. Amplification of AC133 gene transcript was performed using RT-PCR kit (Invitrogene, San Diego, Calif.) according to the manufacturer's instructions. Through screening, the PCR™ primer sequences used in the experiment were forward primer 5'-tgtacgaattcgacagctacttggctca-gac-3' (SEQ ID NO:1) and reverse primer 5'-tctagctcgag-catgatctttatgataacc-3' (SEQ ID NO:2). The expected PCR™ product was 670 bp which is sequence verified. The primers were designed based on the AC133 gene sequence with GeneBank ID:AF027208. Quantitative PCR™ to β-actin was performed as an additional control. Patients 1 and 2 had metastatic disease; patient 3 had resected Duke C cancer three weeks prior.

As cancer has risen to the forefront of highly-studied human diseases, a pressing need has developed for practical, noninvasive and economical means for detecting and/or diagnosing cancer, and monitoring the effectiveness of anti-angiogenic therapy. The use of antiangiogenic therapy has been demonstrated in patients with metastatic colorectal cancer. This has further increased the need for serial measurements of anti-angiogenic therapy given that the expense and invasiveness of any particular method is compounded when multiple and frequent measurements must be taken. Available methods of monitoring angiogenic activity, such as microvessel density assay (MVD), have many practical and theoretical limitations for clinical use, as it requires direct assessment of microvessels within the tumor tissue.

Angiogenesis occurs not only through tumor vessel cooption, but also through mobilization and activation of bone marrow derived endothelial progenitors (EPCs) to the sites of active angiogenesis, a feature which MVD fails to assess. Therefore, EPCs are viable angiogenic surrogates and could be quantified with fluorescence-activated cell sorting techniques (FACS) using monoclonal antibodies to AC133. However, there are many limitations of the FACS procedure. For instance, because EPCs are found in low concentrations and give a poor yield during isolation, FACS assays require up to 50–100 mL of blood per assay. This process can be quite burdensome if serial measurements are required. FACS can be highly variable and subject to poor yield and viability of EPCs, as it is believed that EPCs often undergo apoptosis during isolation procedures, lowering their recovery. In addition, FACS sorting is extremely cumbersome and expensive.

Thus, while methods for monitoring angiogenic activity exist, each of these methods have significant limitations.

A. The Present Invention

The present invention provides a single-step, highly sensitive yet specific and quantitative method to detect and quantify EPCs in the human peripheral blood. AC133 is a glycoprotein of undefined function that is highly specific to EPCs, and is present at 0.1–0.5% of a peripheral blood sample of subjects. Because AC133 is highly specific to EPCs, RT-PCR that specifically amplifies the AC133 gene product in a cell sample can be used to estimate the number of EPCs in the sample. This estimate of the quantity of EPCs can be derived using a standardized curve developed from measuring the signal intensity of known quantities of EPCs.

As previously stated, mobilization of EPCs to the sites of angiogenesis is a hallmark of angiogenic activity. Thus, this method of quantitating EPCs also monitors angiogenic activity. Moreover, given the involvement of mobilized EPCs at sites of cancer angiogenesis, the present invention also facilitates the detection angiogenic activities and diagnosis of cancers in which this mobilization occurs, including but not limited to colorectal cancer, bladder cancer, ovarian cancer, testicular cancer, breast cancer, skin cancer, lung cancer, pancreatic cancer, stomach cancer, esophageal cancer, brain cancer, leukemia, liver cancer, endometrial cancer, prostate cancer, and head and neck cancer.

The method is highly reproducible, practical, non-invasive, and suitable for serial measurements, as each assay only requires 5–10 mL of blood. The sensitivity of the assay is evaluated by serial dilution of AC133+ EPCs in the U-937 cell line or enriched peripheral mobilized stem/progenitor in human mononuclear peripheral blood. The detection limit of this procedure is 1 EPC per one million PMNC.

B. AC133, EPCs and Angiogenesis

AC133 is a structurally novel 5-transmembrane glycoprotein with no known function (Yin et al., 1997). It is selectively expressed on the surface of bone marrow-derived endothelial progenitor cells ("EPCs") (Reyes et al., 2002; Schmeisser et al., 2000; Hariharan et al., 1999). The DNA sequence of AC133 can be found at GeneBank ID AF027208 (SEQ ID NO:3).

EPCs are thought to play a role in postnatal angiogenesis (Gill et al., 2001). Emerging evidence suggests that one of the important events in angiogenesis is the mobilization and activation of EPCs to the sites of angiogenesis (Reyes et al., 2001; Gill et al., 2001). For instance, vascular trauma, induced by burn or by mechanical disruption such as during surgical procedures, leads to a cascade of events that include the recruitment of EPCs to the site of injured vascular tissue, accelerating vascular healing (Gill et al., 2001). EPCs also play a role in cancer angiogenesis. Therefore, assessing EPC recruitment and proliferation provides important information in diagnosing these various injuries and diseases. In addition to merely identifying angiogenic activity of cancer, the present invention also may be used for cancer prognosis, identifying angiogenic potential or backgrouned of early or metastatic cancer, assessing tumor burden, predicting tumor recurrence, assessing chemotherapy success and measuring remission.

C. Obtaining Cell Samples

The invention discloses a method comprising, in part, obtaining a cell sample from a human subject. One specific embodiment of the invention involves collection of a sample of peripheral blood from a human subject. This can be accomplished through intravenous withdrawal of blood or other available means from any exterior limb or other vein comprising part of the peripheral circulatory system.

Once the cell sample is collected, the sample must be processed to isolate cells. One aspect of this invention discloses isolation of mononuclear cells. One method to isolate mononuclear cells from blood is the Ficoll-Paque (Pharmacia Biotech) procedure. Ficoll-Paque is a sterile medium used to isolate cells in high yield from peripheral blood. Other methods of isolating cells from peripheral blood include ultracentrifugation and filtration. Collection of buffy coat monolayer cells also may be used.

D. Isolation and Quantitation of RNA Transcripts from the Cell Sample

Once a cell containing sample is obtained, RNA is extracted from the cells. Many methods to isolate total cellular RNA are well know to those skilled in the art. See, for example, Chomczynski and Sacchi (1987). A particular method to accomplish this task is the use of the Trizol reagent (Gibco Life Technologies) to extract total cellular RNA. The Trizol procedure involves homogenization of the cells in a blender followed by extraction with the phenol-based Trizol reagent. The RNA is then precipitated with isopropyl alcohol and washed with ethanol before being redissolved in RNAse-free water or 0.5% SDS.

E. Reverse Transcription

Reverse transcription is a process for the conversion of mRNA into DNA. Briefly, a poly-dT primer is annealed to the poly-A tail of a messenger RNA. This provides a free 3' end for extension by reverse transcriptase (RT). The enzyme performs 5'→3' synthesis, using the mRNA as a template. The intermediate product, a hybrid RNA-DNA molecule, is created. At the end of this reaction, the enzyme "loops back" on itself by using the last few bases of the reverse transcript as a template for synthesis of a complete, i.e., a complementary DNA that displaces the mRNA. This creates a "hairpin" structure. The original mRNA can then be degraded by alkali treatment, producing a single-stranded DNA. The hairpin provides a natural primer for the next step—the use of DNA polymerase I to convert the single-stranded DNA into double-stranded DNA, a cDNA. The hairpin is removed by S1 nuclease.

Methods of reverse transcribing RNA into cDNA are well known and described in Sambrook et al. (1989). Alternative methods for reverse transcription utilize thermostable, RNA-dependent DNA polymerases and are well known to those of skill in the art.

F. Amplification Methodology

1. Primers

In general, nucleic acid amplification methodology relies upon the use of primers, which facilitate the amplification process. The word primer, as defined herein, is meant to encompass any nucleic acid that is capable of priming the synthesis of a nascent nucleic acid in a template-dependent process. Typically, primers are oligonucleotides from ten to twenty-five base pairs in length, but longer sequences can be employed. Primers may be provided in double-stranded or single-stranded form, although the single-stranded form is preferred. Specific embodiments of the present invention disclose primers for use in the amplification reactions.

Multiple primers were created based on complementarity to the AC133 gene product, with GeneBank ID:AF027208. The specific primers disclosed in the invention were selected by screening of multiple primers for optimum results. However, the present invention may be performed using a variety of suitable primers. Oligonucleotide synthesis may be performed according to standard methods. See, for example, Itakura and Riggs (1980). Additionally, U.S. Pat. Nos. 4,659,774, 4,816,571, 5,141,813, 5,264,566, 4,959,463, 5,428,148, 5,554,744, 5,574,146, 5,602,244, each of which is incorporated herein by reference, describe methods of preparing oligonucleotides. In addition, primers are available commercially at affordable rates.

The use of a probe or primer of between 13 and 100 nucleotides, preferably between 17 and 100 nucleotides in length, or in some aspects of the invention up to 1–2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

2. Hybridization

Accordingly, the nucleotide sequences of the invention (such as primers) may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

A medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results. In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

3. Labels

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

4. PCR™

In general, it is envisioned that the probes or primers described herein will be useful as reagents in solution hybridization, as in PCR™, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the specification are incorporated herein by reference.

A number of template dependent processes are available to amplify the AC133 gene product in a given cell sample. One of the best known amplification methods is the polymerase chain reaction (referred to as PCR™) which is described in detail in U.S. Pat. Nos. 4,683,202 and 4,800,159, and in Innis et al., 1990. Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

The reverse transcriptase (RT) PCR amplification procedure is a variant of PCR that permits amplification of mRNA templates. Thus, the preferred method of amplifying the AC133 gene product utilizes a RT-PCR kit (Invitrogene), according to the manufacturer's instructions. This technique uses fluorogenic hybridization probes or dsDNA-specific fluorescent dyes to detect PCR product during amplification (real-time detection) without purification or separation by gel electrophoresis. The sensitivity of this method's probes allows measurement of the PCR product during the exponential phase of amplification before the critical reactants become limiting. This method does not require the separation of the PCR products.

5. Quantitative PCR (i) Types of Quantitative PCR

The present invention relies on quantitative PCR—more specifically, quantitative RT-PCR—to calculate the number of AC133+ cells in a sample. The methods may be semi-quantitative or fully quantitative.

Two approaches, competitive quantitative PCR™ and real-time quantitative PCR™, both estimate target gene concentration in a sample by comparison with standard curves constructed from amplifications of serial dilutions of standard DNA. However, they differ substantially in how these standard curves are generated. In competitive QPCR, an internal competitor DNA is added at a known concentration to both serially diluted standard samples and unknown (environmental) samples. After coamplification, ratios of the internal competitor and target PCR™ products are calculated for both standard dilutions and unknown samples, and a standard curve is constructed that plots competitor-target PCR™ product ratios against the initial target DNA concentration of the standard dilutions. Given equal amplification efficiency of competitor and target DNA, the concentration of the latter in environmental samples can be extrapolated from this standard curve.

In real-time QPCR, the accumulation of amplification product is measured continuously in both standard dilutions of target DNA and samples containing unknown amounts of target DNA. A standard curve is constructed by correlating initial template concentration in the standard samples with the number of PCR™ cycles ($C_t$) necessary to produce a specific threshold concentration of product. In the test samples, target PCR™ product accumulation is measured after the same $C_t$, which allows interpolation of target DNA concentration from the standard curve. Although real-time QPCR permits more rapid and facile measurement of target DNA during routine analyses, competitive QPCR remains an important alternative for target quantification in environmental samples. The coamplification of a known amount of competitor DNA with target DNA is an intuitive way to correct for sample-to-sample variation of amplification efficiency due to the presence of inhibitory substrates and large amounts of background DNA that are obviously absent from the standard dilutions.

Another type of QPCR is applied quantitatively PCR™. Often termed "relative quantitative PCR," this method determines the relative concentrations of specific nucleic acids. In the context of the present invention, RT-PCR is performed on mRNA species isolated from patients. By determining that the concentration of a specific mRNA species varies, it is shown that the gene encoding the specific mRNA species is differentially expressed.

(ii) Theoretical Considerations

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR™ products must be sampled when the PCR™ reactions are in the linear portion of their curves.

The second condition that must be met for a quantitative RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR product, display of the product on an electrophoretic gel or another display method becomes less complex, has less background and is easier to interpret.

6. Other Amplification Procedures

A number of other template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al. (1988), each of which is incorporated herein by reference in their entirety.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al, 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR™" (Frohman, 1994; Ohara et al., 1989).

G. Separation Methods

It is normally desirable, at one stage or another, to separate the amplification products from reagents, such as the template or excess primers, or from other amplification products. For example, amplification products can be separated by agarose, agarose-acrylamide or polyacrylamide gel electrophoresis using standard methods. See Sambrook et al. (1989). When working with nucleic acids, denaturing PAGE is preferred.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

Separated amplification products may be cut out and eluted from the gel for further manipulation. Using low melting point agarose gels, the separated band may be removed by heating the gel, followed by extraction of the nucleic acid.

These separation techniques can be adapted to function in the clinical setting, allowing the processing of large numbers of samples. However, new tools for the separation and detection of PCR™ products allow clinicians to view hundreds or thousands of samples at once. These techniques include FMAT (fluorometric microvolume assay technique), chemiluminescence, sequence detection systems (Applied Biosystems) and mass spectroscopy.

The following are a few examples of separation techniques readily applied to nucleic acids.

1. Gel electrophoresis

In one embodiment, amplification products are separated by agarose, agarose-acrylamide or polyacrylamide gel electrophoresis using standard methods (Sambrook et al., 1989).

2. Chromatographic Techniques

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982). In yet another alternative, labeled cDNA products, such as biotin-labeled or antigen-labeled can be captured with beads bearing avidin or antibody, respectively.

3. Microfluidic Techniques

Microfluidic techniques include separation on a platform such as microcapillaries, designed by ACLARA Biosciences Inc., or the LabChip™ "liquid integrated circuits" made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR™ apparatus for collection and amplification of nucleic acids from a specimen. U.S. Pat. No. 5,304,487 to Wilding et al., and U.S. Pat. No. 5,296,375 to Kricka et al., discuss devices for collection and analysis of cell containing samples and are incorporated herein by reference. U.S. Pat. No. 5,856,174 describes an apparatus which combines the various processing and analytical operations involved in nucleic acid analysis and is incorporated herein by reference.

4. Capillary Electrophoresis

In some embodiments, it may be desirable to provide an additional, or alternative means for analyzing the amplified genes. In these embodiment, microcapillary arrays are contemplated to be used for the analysis.

Microcapillary array electrophoresis generally involves the use of a thin capillary or channel which may or may not be filled with a particular separation medium. Electrophoresis of a sample through the capillary provides a size based separation profile for the sample. The use of microcapillary electrophoresis in size separation of nucleic acids has been reported in, e.g., Woolley and Mathies (1994). Microcapillary array electrophoresis generally provides a rapid method for size-based sequencing, PCRT™ product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Microfabrication of microfluidic devices including microcapillary electrophoretic devices has been discussed in detail in, e.g., Jacobsen et al. (1994); Harrison et al. (1993); Manz et al. (1992); and U.S. Pat. No. 5,904,824. Typically, these methods comprise photolithographic etching of micron scale channels on a silica, silicon or other crystalline substrate or chip, and can be readily adapted for use in the present invention. In some embodiments, the capillary arrays may be fabricated from the same polymeric materials described for the fabrication of the body of the device, using the injection molding techniques described herein.

Tsuda et al. (1990), describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acids in the sample.

H. Detection of Nucleic Acids

In accordance with the present invention, a nucleic amplification product will be detected and quantified. In certain applications, the detection may be performed by visual means. A typical visualization method involves staining of a gel with ethidium bromide and visualization of bands under UV light. Alternatively, if the amplification products are integrally labeled with radio- or fluorometrically-labeled nucleotides, the separated amplification products are subjected to radioactive scintigraphy of incorporated radiolabel or fluorescent detection, or using electrical and/or thermal impulse signals (Affymax technology; Bellus, 1994).

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In traditional methods, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

1. Mass Spectroscopy

A recent innovation in nucleic acid detection is mass spectrometry. Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Other applications of mass spectrometric methods known in the art can be found summarized in Methods in McCloskey (1990).

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Reviews summarizing this field include Schram (1990); and Crain (1990). The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Koster et al., 1987).

Two ionization/desorption techniques are electrospray/ionspray (ES) and matrix-assisted laser desorption/ionization (MALDI). ES mass spectrometry was introduced by Fenn et al. (1989); WO 90/14148 and its applications are summarized in review articles (Smith et al., 1990; Ardrey, 1992). As a mass analyzer, a quadrupole is most frequently used. The determination of molecular weights in femtomole amounts of sample is very accurate due to the presence of multiple ion peaks which all could be used for the mass calculation.

MALDI mass spectrometry, in contrast, can be particularly attractive when a time-of-flight (TOF) configuration is used as a mass analyzer. The MALDI-TOF mass spectrometry has been introduced by Hillenkamp et al. (1990). Since, in most cases, no multiple molecular ion peaks are produced with this technique, the mass spectra, in principle, look simpler compared to ES mass spectrometry. DNA molecules up to a molecular weight of 410,000 daltons could be desorbed and volatilized (Williams et al., 1989). More recently, the use of infra red lasers (1R) in this technique (as opposed to UV-lasers) has been shown to provide mass spectra of larger nucleic acids such as, synthetic DNA, restriction enzyme fragments of plasmid DNA, and RNA transcripts up to a size of 2180 nucleotides (Berkenkamp et al., 1998). Berkenkamp et al. (1998) also describe how DNA and RNA samples can be analyzed by limited sample purification using MALDI-TOF IR.

In Japanese Patent 59-131909, an instrument is described which detects nucleic acid fragments separated either by electrophoresis, liquid chromatography or high speed gel filtration. Mass spectrometric detection is achieved by incorporating into the nucleic acids atoms which normally do not occur in DNA such as S, Br, I or Ag, Au, Pt, Os, Hg.

2. Energy Transfer

Another emerging method for detecting nucleic acids involves energy transfer. Labeling hybridization oligonucleotide probes with fluorescent labels is a well known technique in the art and is a sensitive, non-radioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed (Forster, 1948). The distance between donor and acceptor dyes at which energy transfer efficiency is 50% is referred to as the Forster distance ($R_o$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label. Several formats for FET hybridization assays are reviewed in Nonisotopic DNA Probe Techniques (1992).

Homogeneous methods employing energy transfer or other mechanisms of fluorescence quenching for detection of nucleic acid amplification have also been described. Higuchi, disclose methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. Lee et al. (1993) disclose a real-time detection method in which a doubly-labeled detector probe is cleaved in a target amplification-specific manner during PCR™. The detector probe is hybridized downstream of the amplification primer so that the 5'-3' exonuclease activity of Taq polymerase digests the detector probe, separating two fluorescent dyes which form an energy transfer pair. Fluorescence intensity increases as the probe is cleaved. PCT Application WO 96/21144 discloses continuous fluorometric assays in which enzyme-mediated cleavage of nucleic acids results in increased fluorescence. Fluorescence energy transfer is suggested for use in the methods, but only in the context of a method employing a single fluorescent label which is quenched by hybridization to the target.

Signal primers or detector probes which hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. The secondary amplification products generated from signal primers may be detected by means of a variety of labels and reporter groups, restriction sites in the signal primer which are cleaved to produce fragments of a characteristic size, capture groups, and structural features such as triple helices and recognition sites for double-stranded DNA binding proteins.

Many donor/acceptor dye pairs known in the art and may be used in the present invention. These include, for example, fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms it is only necessary that the emission wavelengths of the donor fluorophore overlap the excitation wavelengths of the acceptor, i.e., there must be sufficient spectral overlap between the two dyes to allow efficient energy transfer, charge transfer or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Any dye pair which produces fluorescence quenching in the detector nucleic acids of the invention are suitable for use in the methods of the invention, regardless of the mechanism by which quenching occurs. Terminal and internal labeling methods are both known in the art and maybe routinely used to link the donor and acceptor dyes at their respective sites in the detector nucleic acid.

I. Kits

The invention may also comprise a kit to perform any of the methods described herein. In a non-limiting example, primers, enzymes for reverse transcription, enzymes for amplification and additional agents, may be comprised in a kit. The kits will thus comprise one or more of these reagents in suitable container means. The kits may also comprise agents for RNA isolation, purification of amplification products, labels, etc.

The components of the kits may be packaged either in aqueous media or in lyophilized form. The suitable container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the reagent containers in close confinement for commercial sale. Such containers may include injection or blow-molded plastic containers into which the desired vials are retained.

J. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Quantitative PCR™ of AC133. mRNA were prepared from $1 \times 10^6$ human peripheral mononuclear cells and extracted using oligo dT. A number of specific 3' and 5' primers for AC133 were designed based on the gene bank sequence query on published cDNA of AC133 (Yin et al., 1997). Through screening, highly specific 3' and 5' primers were selected. All PCR™ for AC133 was performed under standard protocols with amplification for 30 cycles and with β-actin as an internal control. The sensitivity of the assay was evaluated by serial dilution of human umbilical cord endothelial cells in the U-937 cell line or purified CD34+ cells in human mononuclear peripheral blood. The detection limit of this procedure was 1 EPC per $1 \times 10^6$ PMNC and specificity is more than 90%.

Measurement of CECs and EPCs. Measurement of cells in the peripheral blood is enumerated by three-color flow cytometry using a panel of monoclonal antibodies that react with CD45 (to exclude hematopoietic cells), AC133, and CD34. Appropriate analysis gates were used to enumerate EPCs (Boyer et al., 2000). Reference fluorescent beads are used to calculate the absolute cell numbers. After acquisition of at least 100,000 cells per peripheral blood sample, informative analyses are obtained by collecting adequate numbers of events (>100, typically 3–400) in the CEC enumeration gates. Sensitivity and specificity of the procedure can be evaluated by serial dilution of human cytokine mobilized CD34+ enriched MNC preparations and in the U-937 cell lines. The detection limit of this procedure is 0.1 cell/µL, and specificity is more than 90% (Boyer et al., 2000).

Example 2

Results

RT-PCR was performed in three patients with CRC, as well as two healthy volunteers to analyze AC133 expression. The control was from enriched peripheral mononuclear progenitors/stem cells prepared for bone marrow transplant with CD34+ at $1 \times 10^6$ MNC. It is interesting to note that both patients 1 and 2 had metastatic disease, whereas patient 3 had the primary tumor resected approximately 4 wk previously, and showed lower level AC133 as well as plasma VEGF level (FIG. 1). The data indicates decrease in tumor burden (surgery) is associated with decreased peripheral blood EPCs.

Serum VEGF and other angiogenic cytokines. Cytokines and VEGF were measured in the plasma of the human subjects by using commercial ELISA kits for VEGF and others cytokines (R&D, Minneapolis, Minn.) as described elsewhere (Shi et al., 2001; Shi et al., 2000).

Figure 2:
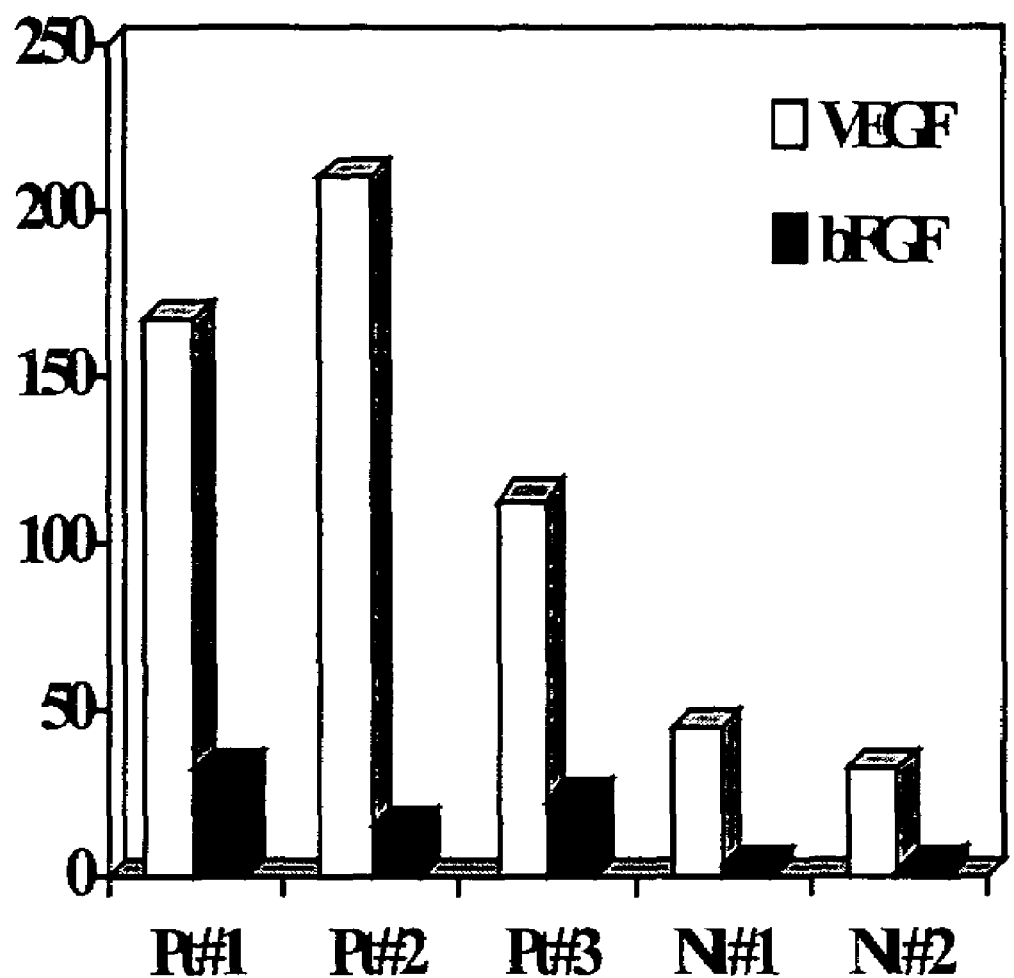
FIG. 2. Levels of VEGF and bFGF are significantly elevated in cancer patients as compared to normal controls.

ELISA assays were conducted for VEGF and basic FGF in the plasma samples from the three CRC patients and two healthy normal volunteers. The data (FIG. 2) shows that plasma VEGF and FGF are significantly elevated as compared to that of the normal volunteers. The VEGF level appeared to positively correlate with AC133 signals in all three patients (FIG. 1). Furthermore, patients 1 and 2 are CRC patients with metastatic disease and appeared to exhibit higher levels of AC133 and plasma VEGF than patient 3, the resected Duke C colon cancer. Other plasma angiogenic cytokines, e.g., nitric oxide, will be explored for alternative hypothesis using the methods as previously described (Shi et al., 2001; Shi et al., 2000).

Example 3

RT-PCR and Quantitative PCR™ (Q-RT-PCR) Analysis of AC133

Study population. Fifty-eight CRC patients were enrolled in this study. Patients with underlying active wound, inflammation, infection, surgery <4 weeks, recent heart attack or stroke, or limb ischemia were not eligible. All patients were required to sign an informed consent before 30 cc of peripheral blood is collected.

CEP positive control cells. Cytokine mobilized CD34+ PBMNC from healthy volunteers were used in this experiment. The frozen CD34+ enriched peripheral blood mononuclear cells preparations were thawed in 37° C. water bath. The red blood cells were lysed with RBC lysates. PBMNC cells were then incubated with 1.5 μL of FITC-labeled high-affinity, nonneutralizing MoAbs to a phycoerythrin (PE; red fluorescence)-labeled anti-CD34 antibody (Becton Dickinson, San Jose, Calif.) for 20 minutes and the cells were washed with PBS. The number of positive cells was compared to immunoglobulin G isotype control (FITC; Immunotech, Marceille, France) and determined using Coulter Elite flow cytometer (COULTER, Hialeah, Fla.). Nonviable cells were identified by 7AAD (viablity marker) with propidium iodide staining. A total of at least 10,000 events were acquired. The CD34+ cells were present in 0.56% of the total PBMNC. The CD34+, 7AAD(−) population was 96.1%.

Figure 3:
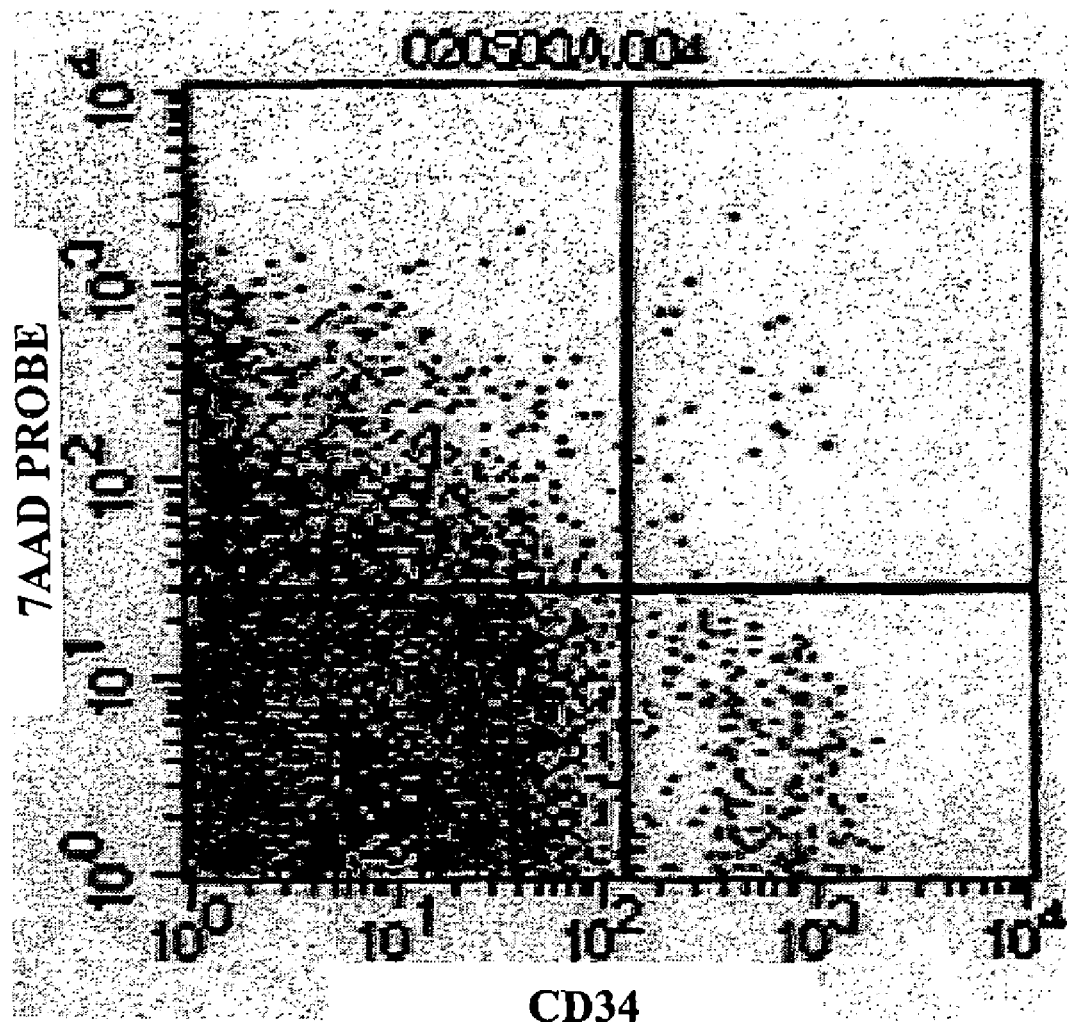
FIG. 3. Viability of CD34+ cells expressing the AC133 (CD133) marker.
Figure 4:
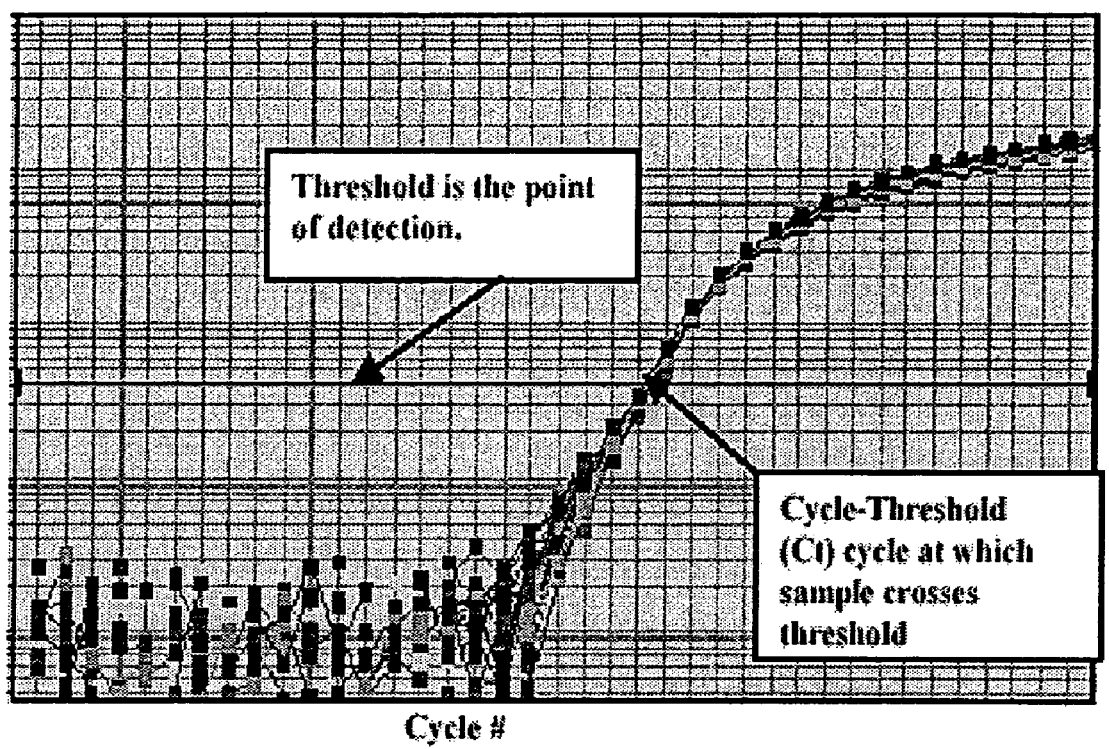
FIG. 4. RT-PCR showing elevated levels of AC133 in patient samples. The amount of target, normalized to an endogenous reference (GAPDPH) and relative to the calibrator is defined by the $\Delta\Delta Ct$ method.
Figure 5:
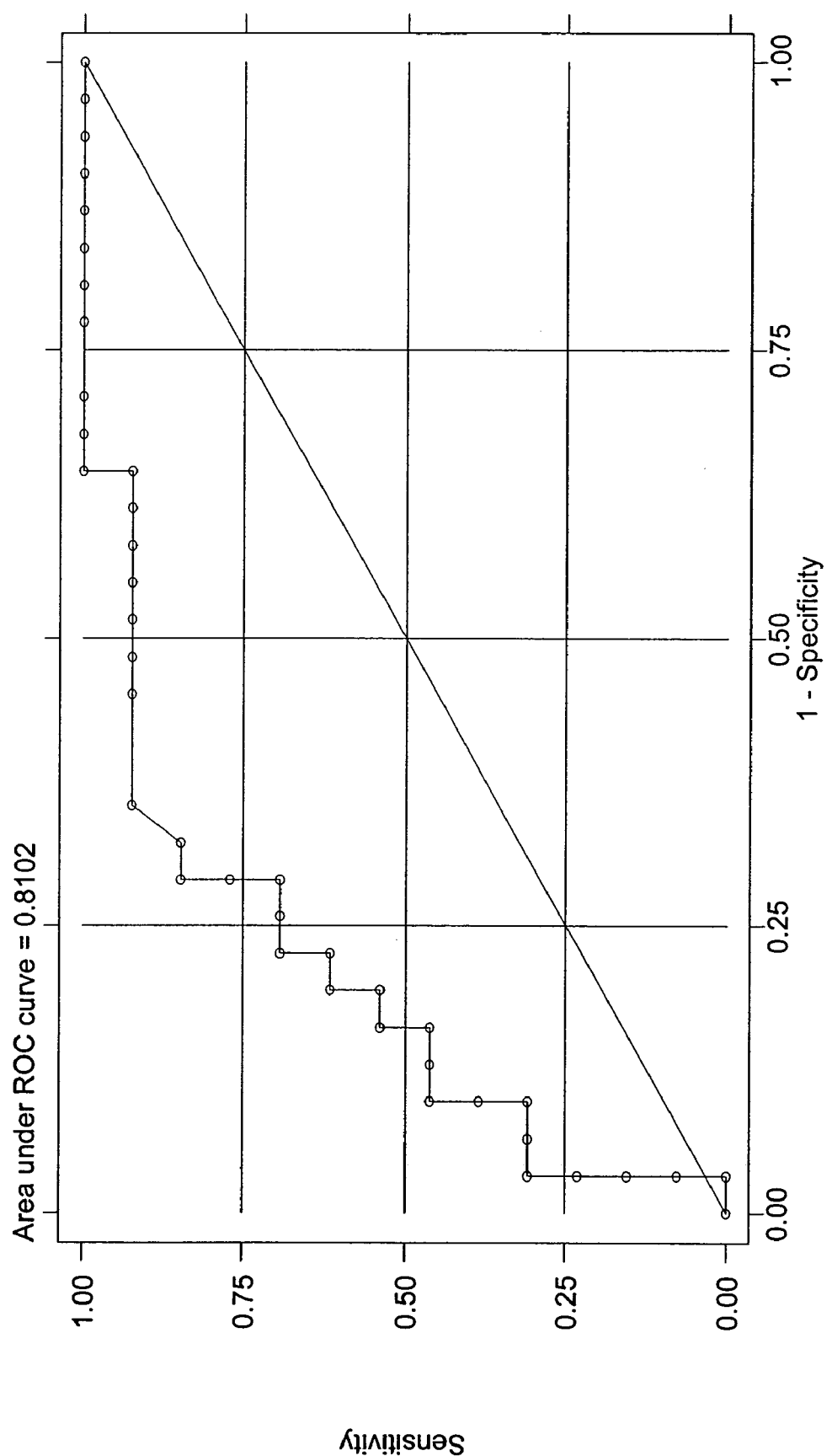
FIG. 5. Sensitivity and specificity of quantitative PCR (Q-RT-PCR). In CRC patient samples the estimated CD133 threshold that distinguishes active or inactive disease status appeared to be at 0.017 with an area under the curve (AUC) of 81%. Sample size (n=50).

RT-PCR. RT-PCR was performed in patients with β-actin as the control. The amplified product of 670 bp has been sequence verified and AC133 was found to be present only in patients but not in normal controls. FIG. 3 shows the level of AC133 elevated in some patients samples. These results were confirmed in additional studies using other patient samples.

PCR™ was performed in a total volume of 50 μl containing 1× TaqMan buffer, 5.5 nM MgCl2, 200 μM dATP, dCTP, dGTP and 400 μM dUTP, 300 nM each primer, 100 nM probe, 0.5 units of AmpErase Uracril N glycosilase (UNG), 1.25 units AmpliTaq Gold, and 10 μl of cDNA. Both α-actin and AC133 amplification were performed in duplicate for each sample. The thermal cycle conditions included 2 at 50° C. and 10 min at 95° C., followed by 40 cycles of 95° C. for 15 and 60° C. for 1 min. All reagents used for RT-PCRT were purchased from Applied Biosystems (Foster City, Calif.). Primers used were:

```
AC133: Left:  AGCCTTCATCCACAGATGCT       (SEQ ID NO:5)
       Right: TTTTGGATTCATATGCCTTCTG     (SEQ ID NO:6)
GAPDH: Left:  CTTCACCACCATGGAGAAGGC      (SEQ ID NO:7)
       Right: GGCATGGACTGTGGTCATGAG      (SEQ ID NO:8)
```

Data interpretation. The amount of target normalized to an endogenous reference (GAPDH) and relative to the positive control is defined by the $C_t$ method. The formula is applied as follows:

$$\text{Target amount} = 2^{-\Delta\Delta C_t}$$

where $\Delta\Delta C_t = \{[C_t(\text{AC133 sample}) - C_t(\text{GAPDH sample})] - [C_t(\text{AC133 calibrator}) - C_t(\text{GAPDH calibrator})]\}$.

Real-time QRT-PCR of AC133 (CD133). Real time quantitative-RT-PCR was conducted using AC133 primers to quantify CEP. The assays were performed based on TaqMan methodology, using the ABI PRISM 7700 sequence detection system (Applied Biosystems). Through fluorescence emission, this technique allows the cycling point to be found when the PCR™ product is detectable ($C_t$ value correlates with the starting quantity of the target mRNA. The primers used were as follows:

```
AC133:
Left:  CATGTTTGGAGGATCTTGCTAGC    (SEQ ID NO:9)
Right: TTCCCGCACAGCCCC            (SEQ ID NO:10)
Probe: ATGGCCCTCGTACTCGGCTCCC     (SEQ ID NO:11)

GAPDH:
Left:  CTTCACCACCATGGAGAAGGC      (SEQ ID NO:12)
Right: GGCATGGACTGTGGTCATGAG      (SEQ ID NO:13)
Probe: CCTGGCCAAGGTCATCCATGACAACTTT (SEQ ID NO:14)
```

Peripheral blood samples were collected after informed consent and the results were blinded until analysis. Patients who had surgery less than 4 weeks, active arthritis, trauma and/or inflammation were excluded from this study. The assay was based on the methods described by Marchetti et al. (2002) except GAPDH was used as the internal control. All samples were run in duplicate with AC133+ cells from cytokine mobilized peripheral stem cells served as positive control. CD133 mRNA was detected only in the peripheral blood of active CRC patients but not in that of healthy volunteers. (n=10).

Real time Q-RT-PCR of AC133 were performed in patients with or without active CRC (n=44). The estimated median value of AC133 marker was significantly higher in patients with clinical disease (4.2; range: 0.017–106.9) as compared to those with no clinical disease (0.0017, range, 0.0–9.51); p value<0.001 (Mann-Whitney test). When three median AC133 values (0.01, 0.05, 0.1), were used as cut-off points to estimate the odds ratio (OR) and 95% confidence interval (CI) distinguishing active or inactive radiographic disease status, all three points were statistically significant OR ranging from 8.2–14.6 (Table 1).

It is interesting to note that AC133 was elevated in three patients with rising CEA but no evidence of CRC. CEP was also elevated in patients with relapsed CRC, a condition reflected by elevated CEA. One patient had rising CEA due to thyroid cancer. Two high-risk patients with history of resected liver metastasis had elevated AC133 up to 9. The estimated AC133 cutoff point that distinguishes active or inactive disease status appeared to be at 0.017 with AUC of 81% (FIG. 6). This study showed that real time Q RT-PCR of AC133 correlate with the tumor status as a result of the underlying tumor angiogenesis and can be used as a surrogate marker of tumor angiogenesis.

TABLE 1

| Results | CD133 Cutoff point (equal to or greater) | | |
|---|---|---|---|
| | 0.01 | 0.05 | 0.1 |
| Clinical active CRC | | | |
| No (N = 31) | 14 (45.2) | 9 (29) | 9 (29) |
| Yes (N = 13) | 12 (92.3) | 11 (84.6) | 10 (76.9) |
| Odd Ratio | 14.6 | 13.4 | 8.2 |
| (95% CI) | 1.7–126.2 | (2.5–73.2) | (1.8–36.7) |
| P value | 0.004 | 0.001 | 0.005 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

K References

The following references, to the extent that they provide exemplary procedural or other details supplementary to those set forth herein, are specifically incorporated herein by reference.

U.S. Pat. No. 4,659,774
U.S. Pat. No. 4,683,195
U.S. Pat. No. 4,683,202
U.S. Pat. No. 4,800,159
U.S. Pat. No. 4,816,571
U.S. Pat. No. 4,883,750
U.S. Pat. No. 4,959,463
U.S. Pat. No. 5,141,813
U.S. Pat. No. 5,264,566
U.S. Pat. No. 5,279,721
U.S. Pat. No. 5,296,375
U.S. Pat. No. 5,304,487
U.S. Pat. No. 5,428,148
U.S. Pat. No. 5,547,861
U.S. Pat. No. 5,554,744
U.S. Pat. No. 5,574,146
U.S. Pat. No. 5,602,244
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,856,174
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,900,481
U.S. Pat. No. 5,904,824
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
European Appl. 329 822
European Appl. 320 308
GB Appl. 2 202 328
Japanese Appl. 59-131909
PCT Appl. WO 96/21144
PCT Appl. WO 90/14148
PCT Appl. WO 88/10315
PCT Appl. WO 90/07641
PCT Appl. WO 89/06700
PCT Appl. WO 94/05414
PCT Appl. US87/00880
PCT Appl. US89/01025

Ardrey, In: *Electrospray Mass Spectrometry*, Spectroscopy Europe, 4:10–18, 1992.
Asahara et al., *EMBO J.*, 18:3964–3972, 1999.
Asahara, *Circulation Res.*, 85:221–228, 1999.
Bellus, *J Macromol. Sci. Pure Appl. Chem.*, A31(1): 1355–1376, 1994.
Berkenkamp et al., *Science*, 281(5374):260–262, 1998.
Boyer et al., *J Vasc. Surg.*, 31(1—1):181–189, 2000.
Byrne and Bundred, *Biological Markers*, 15:334–339, 2000.
Byrne Intl. *J. Biol. Markers*, 15:334–339, 2000.
Chomczynski and Sacchi, *Anal. Biochem.*, 162(1):156–159, 1987.
Crain, *Methods Enzymol.*, 193:857–865, 1990.
Fenn et al., *Science*, 246(4926):64–71, 1989.
Folkman et al., *Thrombosis Haemostasis*, 86:23–33, 2001.
Forster, *Ann. Phys.*, 2:55–75, 1948.
Freifelder, In: *Physical biochemistry applications to biochemistry and molecular biology*, 2nd Freeman and Co., NY, 1982.
Frohman, *PCR Methods Appl.*, 4(1):S40–58, 1994.
Gill et al., *Circ. Res.*, 88(2):167–174, 2001.
Gunsilius, *Lancet.*, 357:1449–1450, 2001.
Hariharan et al., *AIDS Res. Hum. Retroviruses*, 15(17): 1545–1552, 1999.
Harrison et al., *Science*, 261:895–897, 1993.
Hillenkamp et al., *Methods Enzymol.*, 193:280–295, 1990.
Hurvitz et al., In: *Honoring People with Cancer*, PRO ASCO Conference, Chicago, Ill., abst # 3536, 2003.
Innis et al., *PCR Protocols*, Academic Press, Inc., San Diego Calif., 1990.
Itakura and Riggs, *Science*, 209:1401–1405, 1980.
Jacobsen et al., *J. Biol. Chem.*, 269(11):8376–82, 1994.
Koster et al. *Biomedical Environmental Mass Spectrometry*, 14:111–116, 1987.
Kwoh et al., *Proc. Natl. Acad. Sci. USA*, 86:1173, 1989.
Lee et al., *Nuc. Acids Res,*. 21, 3761–3766, 1993.
Manz et al., *J Chromatogr.*, 593:253–258, 1992.
Marchetti et al., *Lab. Invest.*, 82(6), 2002.

McCloskey, In: *Mass spectrometry*, Methods in Enzymology, Vol. 193, Academic Press, NY, 1990.
Mundhenke et al., *Clinical Cancer Res.*, 7:3366–3374, 2001.
Ohara et al., *Proc. Natl. Acad. Sci. USA*, 86:5673–5677, 1989.
Rafii, *Nature Revi. Cancer*, 2:826, 2002.
Reyes et al, *Blood*, 98:2615–2625, 2001.
Reyes et al., *J. Clin. Invest.*, 109(3):337–346, 2002.
Sambrook et al., In: *Molecular cloning*, Cold Spring Harbor Laboratory Press, Cold Spring Harbor, N.Y., 1989.
Schmeisser et al., *Cardiovascular Res.*, 49:671–680, 2001.
Schram, *Methods Biochem. Anal.*, 34:203–287, 1990.
Shi et al., *Cancer Res.*, 60:2579–2583, 2000.
Shi et al., *Oncogene*, 20:3751–3761, 2001.
Smith et al., *Anal. Chem.*, 62, 882–89, 1990.
Takahashi, *Nature Med.*, 5:434–438, 1999.
Tsuda et al., *Anal. Chem.*, 62:2149–2152, 1990.
Walker et al., *Proc. Natl. Acad. Sci. USA*, 89:392–396 1992.
Williams et al., *Proc. Natl. Acad. Sci. USA*, 86(14):5537–5541, 1989.
Woolley and Mathies, *Proc. Natl. Acad. Sci. USA*, 91(24):11348–11352, 1994.
Yin et al., *Blood*, 90:5002–5012, 1997.

What is claimed is:

1. A method for diagnosing colorectal cancer in a human subject having colorectal cancer or at risk of developing colorectal cancer comprising:
   (a) obtaining a peripheral blood sample of said subject;
   (b) obtaining RNA transcripts from peripheral blood mononuclear cells of said sample;
   (c) performing quantitative polymerase chain reaction on said RNA using primers that amplify an AC133 nucleic acid segment; and
   (d) comparing the amount of AC133 amplification product with the amount of amplification product in a non-cancer, control sample of peripheral blood mononuclear cells, wherein an increase in the amount of AC133 amplification product in peripheral blood mononuclear cells of said subject, as compared to the amount of AC133 amplification product in the non-cancer, control sample of peripheral blood mononuclear cells, indicates that said subject has colorectal cancer.

2. The method of claim 1, wherein said cells are isolated from a human subject previously diagnosed with cancer.

3. The method of claim 1, wherein forward said primer is composed of the DNA sequence: 5'-tgtacgaattcgacagctact-tggctcagac-3' (SEQ ID NO:1).

4. The method of claim 1, wherein reverse said primer is composed of the DNA sequence: 5'-tctagctcgagcatgatctttat-gataacc-3' (SEQ ID NO:2).

5. The method of claim 1, wherein said increase of AC133 amplification product further predicts tumor burden.

6. The method of claim 1, wherein said increase of AC133 amplification product further predicts tumor relapse.

7. The method of claim 1, further comprising making a treatment decision based on the increase in the amount of AC133 amplification product in cells of said subject.

8. The method of claim 1, further comprising treating said subject for cancer.

9. The method of claim 8, wherein said subject is treated with radiotherapy, immunotherapy, chemotherapy, hormonal therapy or gene therapy.

* * * * *